United States Patent [19]

Ducep et al.

[11] 4,225,589
[45] Sep. 30, 1980

[54] DAUNORUBICIN DERIVATIVES

[75] Inventors: Jean-Bernard Ducep, Paris; Daniel Farge, Thiais; Gérard Ponsinet, Sucy-en-Brie; Daniel Reisdorf, Thiais, all of France

[73] Assignee: Rhone-Poulenc Industries, Paris, France

[21] Appl. No.: 849,761

[22] Filed: Nov. 9, 1977

Related U.S. Application Data

[63] Continuation-in-part of Ser. No. 740,769, Nov. 10, 1976, abandoned.

[30] Foreign Application Priority Data

Nov. 12, 1975 [FR] France ............................ 75 34450
Sep. 27, 1976 [FR] France ............................ 76 28977
Sep. 27, 1976 [FR] France ............................ 76 28978

[51] Int. Cl.² .................... A61K 31/70; C07G 11/00
[52] U.S. Cl. ................................ 424/180; 536/17 A
[58] Field of Search ...................... 536/17 A; 424/180

[56] References Cited

U.S. PATENT DOCUMENTS 4,031,211  6/1977  Patelli et al. ................ 536/17 A

OTHER PUBLICATIONS

American Druggist, May 19, 1969, (Pharm. & Med. Science, pp. 33-34).
Journ. Med. Chem., 1974, vol. 17, No. 3, pp. 335-337.
Experientia 26, 4, pp. 389-390 (1970).
Merck Index, 9th Edition, 1976, No. 3428.

*Primary Examiner*—Ethel G. Love

*Attorney, Agent, or Firm*—Stevens, Davis, Miller & Mosher

[57] ABSTRACT

Daunorubicin derivatives of the formula:

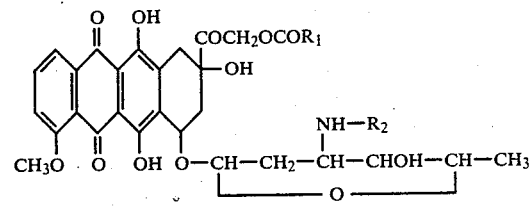

wherein $R_1$ represents a group of the formula:

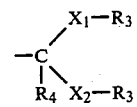

in which (i) $X_1$ and $X_2$ both represent oxygen or both represent sulphur and the symbols $R_3$ each represent alkyl of 1 through 4 carbon atoms, phenyl or phenyl substituted in the para-position by methyl, methoxy or methylthio, or together form an alkylene radical of 2 through 4 carbon atoms, or (ii) one of $X_1$ and $X_2$ represents oxygen and the other represents sulphur and the symbols $R_3$ together form an alkylene radical of 2 through 4 carbon atoms, and $R_4$ represents hydrogen, alkyl of 1 through 4 carbon atoms or phenyl, and $R_2$ represents hydrogen or trifluoroacetyl, are new compounds possessing anti-tumour properties.

20 Claims, No Drawings

DAUNORUBICIN DERIVATIVES

This application is a continuation-in-part of copending application Ser. No. 740,769, filed Nov. 10, 1976, now abandoned.

This invention relates to new derivatives of daunorubicin, to processes for their preparation and pharmaceutical compositions containing them.

The new derivatives of daunorubicin of the present invention are those compounds of the general formula:

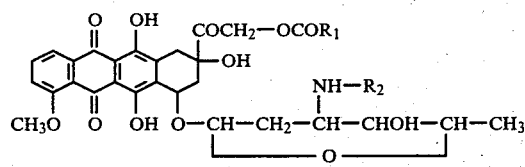

wherein $R_1$ represents a group of the general formula:

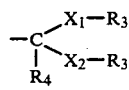

in which (i) $X_1$ and $X_2$ both represent oxygen atoms or both represent sulphur atoms and the symbols $R_3$ each represent an alkyl radical containing 1 to 4 carbon atoms, a phenyl radical or a phenyl radical substituted in the para-position by a methyl, methoxy or methylthio radical; or together form an alkylene radical containing 2 to 4 carbon atoms, or (ii) one of $X_1$ and $X_2$ represents an oxygen atom and the other represents a sulphur atom and the symbols $R_3$ together form an alkylene radical containing 2 to 4 carbon atoms; and $R_4$ represents a hydrogen atom, an alkyl radical containing 1 to 4 carbon atoms or a phenyl radical, and $R_2$ represents a hydrogen atom or a trifluoroacetyl radical, and—when $R_2$ represents a hydrogen atom—acid addition salts, preferably hydrochlorides, thereof.

According to a feature of the invention, the compounds of general formula I, wherein $R_2$ represents a hydrogen atom, are prepared by the process which comprises reacting an alkali metal salt or an alkaline earth metal salt of an acid of the general formula:

$$R_1-COOH \qquad III$$

(wherein $R_1$ is as hereinbefore defined) with a daunorubicin derivative of the general formula:

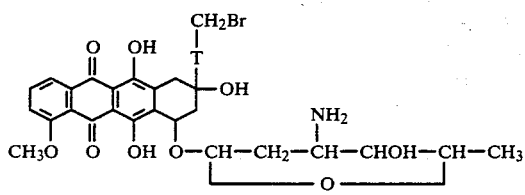

wherein T represents the —CO— radical or a grouping —C(OCH$_3$)$_2$—, or an acid addition salt thereof.

Generally the hydrochloride of the daunorubicin derivative of general formula IV is used, and the reaction is carried out in a polar solvent such as a ketone (e.g. acetone or methyl isobutyl ketone), an alcohol (e.g. methanol or ethanol) or dimethylformamide, or a mixture of these solvents such as a mixture of acetone and ethanol, at a temperature of from 20° to 70° C.

The daunorubicin derivative of general formula IV wherein T represents the grouping —C(OCH$_3$)$_2$— (in the form of an acid addition salt) can be obtained by bromination of an acid addition salt of daunorubicin of the formula:

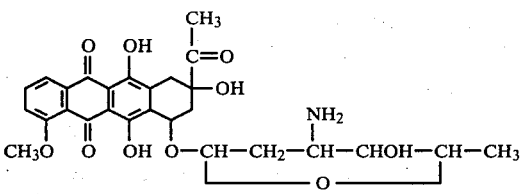

in the presence of methanol. The resulting acid addition salt of the daunorubicin derivative of general formula IV can, if desired, be converted into the free base by methods known per se, for example by dissolving the salt in water and adding an aqueous solution of sodium bicarbonate.

Bromination of the compound of general formula V is generally effected by the action of bromine, phenyltrimethylammonium perbromide, pyridinium perbromide or of pyrrolid-2-one hydrotribromide, in a solvent, such as dioxan or methanol, at a temperature of from 20° to 50° C. The bromination can also be effected by the action of dioxan dibromide, prepared separately before the reaction.

Daunorubicin, its preparation and its physicochemical characteristics have been described in the specification of British Pat. No. 985598 granted to Rhone-Poulenc S.A. on an application filed May 16, 1963. In that specification the antibiotic is designated by 13057 RP.

The daunorubicin derivative of general formula IV wherein T represents the —CO— radical can be obtained by deketalisation of the corresponding compound of general formula IV wherein T represents the grouping —C(OCH$_3$)$_2$—. The deketalisation is generally effected in the presence of hydrochloric acid and of a ketone such as acetone or cyclohexanone.

It is not necessary to isolate the compound of general formula IV wherein T represents the grouping —C(OCH$_3$)$_2$— in order to effect this deketalisation.

The acids of general formula III, wherein $R_1$ represents a group of general formula II in which $R_3$ and $R_4$ are as hereinbefore defined and $X_1$ and $X_2$ both represent oxygen atoms or sulphur atoms, except for those acids wherein $X_1$ and $X_2$ represent oxygen atoms and the symbols $R_3$ and $R_4$ represent alkyl radicals containing 1 to 4 carbon atoms, can be prepared in accordance with the method described by I. Minamida et al., Tetrahedron, 24, 5,293 (1968).

The acids of general formula III, wherein $R_1$ represents a group of general formula II in which $X_1$ and $X_2$ represent oxygen atoms and the symbols $R_3$ and $R_4$ each represent an alkyl radical containing 1 to 4 carbon atoms, can be prepared in accordance with the method described by C. G. Wermuth and H. Marx, Bull. Soc. Chim., 732 (1964).

The acids of general formula III, wherein $R_1$ represents a group of general formula II in which $X_1$ and $X_2$ both represent oxygen atoms or one of $X_1$ and $X_2$ represents an oxygen atom and the other represents a sulphur atom, the symbols $R_3$ together form an alkylene radical containing 2 to 4 carbon atoms, and $R_4$ represents a hydrogen atom, an alkyl radical containing 1 to 4 carbon atoms or a phenyl radical, can be prepared by the reaction of the n-butyl ester of an α-keto-acid of the general formula:

$$R_4-CO-COOH \qquad VI$$

(wherein $R_4$ is as hereinbefore defined) with a compound of the general formula:

(wherein A represents an alkylene radical containing 2 to 4 carbon atoms, and the symbols $X_1$ and $X_2$ are just defined above), followed by saponification of the ester obtained by any means hitherto known for the purpose of obtaining an acid from an ester without affecting the remainder of the molecule.

The reaction is generally carried out in an organic solvent such as benzene and—when $X_1$ and $X_2$ represent oxygen atoms—in the presence of para-toluenesulphonic acid at the reflux temperature of the reaction mixture or—when one of the symbols $X_1$ and $X_2$ represents an oxygen atom and the other represents a sulphur atom—in the presence of boron trifluoride ethereate at a temperature of between 20° and 30° C. The saponification of the resulting ester to the acid can be carried out with, for example, sodium hydroxide or potassium hydroxide in an aqueous medium, preferably at the reflux temperature of the reaction mixture.

The acid of general formula VI wherein $R_4$ represents a hydrogen atom can be prepared in accordance with the method described by F. J. Wolf and J. Weijlard, Org. Synth. 35, 18 (1955).

The acids of general formula VI wherein $R_4$ represents an alkyl radical can be prepared in accordance with the method described by R. Barre, Ann. Chim. (10) 9, 235 (1928).

According to another feature of the invention, the daunorubicin derivatives of general formula I, wherein $R_2$ represents the trifluoroacetyl radical, are prepared by the process which comprises reacting a reactive derivative of trifluoroacetic acid, such as the anhydride or the chloride, with a corresponding daunorubicin derivative of general formula I, wherein $R_1$ is as hereinbefore defined and $R_2$ represents a hydrogen atom, in the form of the free base.

The reaction is generally carried out at a temperature of from 20° to 35° C. in a mixture of organic solvents such as a mixture of chloroform and diethyl ether.

The daunorubicin derivatives of general formula I obtained by the aforedescribed processes can optionally be purified by physical methods such as crystallisation or chromatography or by chemical methods such as the formation of acid addition salts of those compounds wherein $R_2$ represents a hydrogen atom, crystallisation of the salts and decomposition of them in an alkaline medium.

The daunorubicin derivatives of general formula I wherein $R_2$ represents a hydrogen atom, can be converted by methods known per se into acid addition salts, for example by reaction of the basic compounds with acids in appropriate solvents, for example alcohols, ethers, ketones or chlorinated hydrocarbons. The salt which is formed is precipitated, if necessary after concentration of its solution, and is isolated by filtration or decantation.

The new daunorubicin derivatives of general formula I, and—when appropriate—their acid addition salts, have valuable anti-tumour properties coupled with a low toxicity.

Their maximum tolerated dose was determined in mice. It is between 0.5 and 30 mg/kg animal body weight for intraperitoneal administration.

The compounds have proved particularly active against graftable tumours of mice; at doses of between 0.25 and 20 mg/kg animal body weight, administered intraperitoneally, against leucaemia L 1210 and leucaemia P 388, and at doses of 1 to 20 mg/kg animal body weight, administered intravenously, against mammary carcinoma and pulmonary carcinoma.

The daunorubicin derivatives of general formula I of particular interest are those wherein $R_1$ represents a group of general formula II in which $X_1$ and $X_2$ both represent oxygen atoms or both represent sulphur atoms and the symbols $R_3$ each represent an alkyl radical containing 1 to 4 carbon atoms, or a phenyl radical optionally substituted in the para-position by a methyl, methoxy, or methylthio radical, or together form an alkylene radical containing 2 or 3 carbon atoms, or one of the symbols $X_1$ and $X_2$ represents an oxygen atom and the other represents a sulphur atom and the symbols $R_3$ together form an alkylene radical containing 2 or 3 carbon atoms, $R_4$ represents a hydrogen atom or a methyl or phenyl radical, and $R_2$ is as hereinbefore defined.

Amongst such compounds, the preferred products are those of general formula I wherein $R_1$ represents a group of general formula II in which $X_1$ and $X_2$ both represent oxygen atoms or both represent sulphur atoms and the symbols $R_3$ each represent an alkyl radical containing 1 to 4 carbon atoms, or a phenyl, p-methylphenyl, p-methoxyphenyl or p-methylthiophenyl radical, or together form an alkylene radical containing 2 or 3 carbon atoms, or one of $X_1$ and $X_2$ represents an oxygen atom and the other represents a sulphur atom and the symbols $R_3$ together form an alkylene radical containing 2 or 3 carbon atoms, $R_4$ represents a hydrogen atom, and $R_2$ represents a hydrogen atom. Examples of such preferred products are 14-(2,2-diethoxy-acetoxy)daunorubicin, 14-(2,2-dibutoxy-acetoxy)daunorubicin, 14-(2,2-diphenoxy-acetoxy)daunorubicin, 14-[2,2-bis-(4-methylphenoxy)acetoxy]daunorubicin, 14-[2,2-bis(4-methoxyphenoxy)acetoxy]daunorubicin, 14-[2,2-bis(4-methylthiophenoxy)-acetoxy]-daunorubicin, 14-(2,2-diethylthio-acetoxy)daunorubicin, 14-(2,2-diphenylthio-acetoxy)daunorubicin, 14-[(1,3-dioxolan-2-yl)carbonyloxy]daunorubicin, 14-[(1,3-dithiolan-2-yl)carbonyloxy]daunorubicin, 14-[(1,3-dithian-2-yl)carbonyloxy]daunorubicin and 14-[(1,3-oxathiolan-2-yl)carbonyloxy]daunorubicin, and acid addition salts thereof.

For therapeutic purposes the daunorubicin derivatives of general formula I may be employed as such or—when appropriate—in the form of non-toxic acid addition salts, i.e. salts containing anions which are relatively innocuous to the animal organism in therapeutic doses of the salts (such as hydrochlorides, sulphates, nitrates, phosphates, acetates, propionates, succinates, benzoates, fumarates, maleates, tartrates, theophyllineacetates, salicylates, phenolphthalinates and methylene-bis-β-hydroxynaphthoates) so that the beneficial physiological properties inherent in the bases are not vitiated by side-effects ascribable to the anions.

The following Examples illustrate the preparation of the new derivatives of daunorubicin of the present invention.

EXAMPLE 1

A mixture of 14-bromodaunorubicin 13-dimethylacetal hydrochloride (2.2 g) and dry sodium 2,2-diethoxy-acetate (2.05 g) in acetone (500 cc) is heated under reflux for 3 hours whilst stirring. The mixture is then allowed to cool, filtered and concentrated to dryness under reduced pressure (20 mmHg). The residue is dissolved in chloroform (100 cc). The solution is washed with a saturated aqueous sodium chloride solution (100 cc), and the aqueous phase is extracted with chloroform (100 cc). The organic phases are dried over sodium sulphate. After combination and filtration, a 1.085 N solution of dry hydrogen chloride in dioxan (2.2 cc) is added to the solution obtained. The mixture is concentrated under reduced pressure (20 mmHg) to about 30 cc. Diethyl ether (150 cc) is added and the precipitate is filtered off and washed with ethyl acetate (2×50 cc) and with diethyl ether (2×50 cc). The red solid is dried under reduced pressure (0.5 mmHg) at 40° C. 14-(2,2-diethoxy-acetoxy)daunorubicin hydrochloride (1.44 g), having the following characteristics, is thus obtained:

$[\alpha]_D^{20} = +186.4 \pm 8°$ (c=0.515, methanol)

Rf=0.58 [silica gel; methylene chloride:methanol:-formic acid:water (88:15:2:1 by volume)].

Analysis: % calculated: C, 55.82; H, 5.68; N, 1.97; O 31.54 Cl, 4.99. % found: C, 54.85; H, 6.04; M, 1.96; Cl, 5.68.

2,2-Diethoxy-acetic acid, from which the sodium 2,2-diethoxy-acetate is prepared in accordance with the usual methods, can be obtained in accordance with the method described by I. Minamida et al., Tetrahedron, 24, 5,293 (1968).

14-Bromodaunorubicin 13-dimethylacetal hydrochloride can be prepared in the following manner:

Daunorubicin hydrochloride (10 g) is dissolved in anhydrous methanol (270 cc) and dioxan (480 cc) is then added. This mixture is heated to 30° C. and a solution of bromine (3 g) in chloroform (25 cc) is poured in whilst stirring. After a brief period during which the reaction is exothermic, the solution is kept at between 25° and 30° C. for two hours. The reaction mixture is then poured into water (2 liters). At this stage the pH is about 3, and under these conditions the dimethylacetal is sufficiently stable to be isolated. The mixture is immediately extracted with chloroform (500 cc followed by 2×200 cc). The pH of the aqueous solution is adjusted to 8 addition of sodium bicarbonate, and the solution is then extracted in four stages with chloroform (2 liters). After drying over sodium sulphate and filtering, the chloroform solution is treated with a 4.8 N solution (2.06 cc) of hydrogen chloride in dry dioxan. The chloroform is evaporated at 30° C. under reduced pressure (20 mmHg) to give a red solid, which is re-suspended and washed with diethyl ether. This insoluble material is taken up in chloroform (100 cc), the solution is filtered to remove a small amount of insoluble matter and the filtrate is evaporated at 30° C. under reduced pressure (20 mmHg). The residue is washed with diethyl ether and then dried under reduced pressure (0.1 mmHg). 14-Bromodaunorubicin 13-dimethylacetal hydrochloride (2.6 g) is thus obtained in the form of a red powder.

$[\alpha]_D^{20} = +148°$ (c=0.4, methanol)

Rf=0.60 [silica gel; methylene chloride:methanol:-formic acid:water (88:15:2:1 by volume)].

EXAMPLE 2

A mixture of 14-bromodaunorubicin hydrochloride (2.5 g) and dry sodium 2,2-diethoxy-acetate (8.5 g) in acetone (2,500 cc) is heated under reflux for 3 hours whilst stirring. The mixture is then concentrated to dryness under reduced pressure (20 mmHg). The residue is taken up in a saturated aqueous sodium bicarbonate solution (150 cc) and extracted with chloroform (6×150 cc). The extract is dried over sodium sulphate, filtered and a 1 N solution of dry hydrogen chloride in dioxan (3.78 cc) is added to the filtered solution. The mixture is concentrated to about 50 cc under reduced pressure (20 mmHg). Ethyl acetate (50 cc) is added, and the precipitate is filtered off and washed with ethyl acetate (2×10 cc) and with diethyl ether (4×20 cc). The red solid is dried under reduced pressure (0.5 mmHg) at 40° C. 14-(2,2-Diethoxy-acetoxy)daunorubicin hydrochloride (2 g) is thus obtained; its characteristics are identical to those of the product of Example 1.

14-Bromodaunorubicin hydrochloride can be prepared in the following manner:

Daunorubicin hydrochloride (20 g) is dissolved in methanol (540 cc). Dioxan (960 cc) is added and the solution is heated to 30° C. A solution (57.2 cc) of bromine (10 g) in chloroform (100 cc) is added all at once and the mixture is stirred at 30° C. for 2 hours. It is then poured into water (2,000 cc) and extracted with chloroform (3×1000 cc).

The organic phase is discarded, and the aqueous phase is treated with a 5% (w/v) aqueous sodium bicarbonate solution (200 cc) and then extracted with chloroform (4×1000 cc). The organic solution is washed with a saturated aqueous solution of sodium chloride (2×1000 cc) and dried over sodium sulphate. It is then filtered, and acetone (200 cc), followed by a 4.8 N solution of dry hydrogen chloride in dioxan (5 cc), are added to the filtrate. After 30 minutes, the precipitate obtained is filtered off. There is thus obtained 14-bromodaunorubicin hydrochloride (12.54 g) which, after recrystallisation from a mixture of chloroform (1000 cc) and methanol (300 cc), has the following characteristics:

$[\alpha]_D^{20} = -97°$ (c=0.226, water)

Rf=0.5 [silica gel; methylene chloride:methanol:formic acid:water (88:15:2:1 by volume)].

EXAMPLE 3

A mixture of 14-bromodaunorubicin hydrochloride (3 g) and dry sodium 2,2-dibutoxy-acetate (4.5 g) in acetone (500 cc) is heated under reflux for 2 hours 30 minutes. After cooling, the mixture is filtered over diatomaceous silica. The filtrate is concentrated under reduced pressure (0.5 mmHg) at 40° C. to a volume of about 50 cc. The red precipitate is filtered off, washed with acetone (2×15 cc) and dried under reduced pressure (0.5 mmHg) at 25° C. The precipitate is dissolved in chloroform (10 cc) and treated with a 0.83 N solution of dry hydrogen chloride in dioxan (3.3 cc). The limpid red solution is concentrated to dryness under reduced pressure (20 mmHg) at 25° C. The red solid obtained is taken up in methanol (5 cc) and diethyl ether (100 cc) is added. The precipitate is filtered off, and washed with ethyl acetate (3×15 cc) and with diethyl ether (15 cc). The red solid is dried under reduced pressure (0.5 mmHg) at 40° C. to give 14-(2,2-dibutoxy-acetoxy)-daunorubicin hydrochloride (1.250 g) having the following characteristics:

$[\alpha]_D^{20} = +155° \pm 9°$ (c=0.416, methanol)

Rf=0.64 [silica gel; methylene chloride:methanol:-formic acid:water (88:15:2:1 by volume)].

Analysis: % calculated: C, 58.00; H, 6.31; Cl, 4.63; N, 1.83; O, 29.23. % found: C, 56.36; H, 6.17; Cl, 5.6; N, 2.19.

Butyl 2,2-dibutoxy-acetate, from which sodium 2,2-dibutoxy-acetate is prepared in the usual manner, can be obtained in accordance with the method described by I. Minamida et al., Tetrahedron, 24, 5,293, (1968).

EXAMPLE 4

A mixture of 14-bromodaunorubicin hydrochloride (5 g) and dry sodium 2,2-diphenoxy-acetate (8.3 g) in acetone (3500 cc) is heated under reflux for 1 hour 45 minutes whilst stirring. After cooling, the reaction mixture is filtered and the solid is washed with acetone (2×50 cc). The filtrate is concentrated under reduced pressure at 40° C. The residue is suspended in methylene chloride (70 cc), filtered off, and washed with methylene chloride (3×20 cc). The red solid obtained is dissolved in chloroform containing 5% by volume of methanol (150 cc). The solution is washed with a 5% (w/v) aqueous sodium bicarbonate solution (2×150 cc), with a saturated aqueous sodium chloride solution (150 cc) and with distilled water (150 cc). The organic phase is dried over sodium sulphate, filtered and concentrated to about 50 cc under reduced pressure (20 mmHg) at 30° C. Diethyl ether (300 cc) is added, and the precipitate is filtered off and washed with diethyl ether (3×50 cc). The red solid is dried under reduced pressure (0.5 mmHg) at 40° C. to give 14-(2,2-diphenoxy-acetoxy)-daunorubicin (1.9 g) having the following characteristics:

$[\alpha]_D^{20} = +173.5° \pm 17°$ (c=0.258, chloroform)

Rf=0.33 [silica gel; methylene chloride:methanol:-formic acid:water (88:15:2:1 by volume)].

Analysis: % calculated: C, 63.97; H, 5.11; N, 1.82; O, 29.10. % found: C, 63.3; H, 5.1; N, 2.08.

Ethyl 2,2-diphenoxy-acetate, from which the sodium 2,2-diphenoxy-acetate is prepared in the usual manner, can be obtained in accordance with the method of I. Minamida et al., Tetrahedron, 24, 5,293 (1968).

EXAMPLE 5

A mixture of 14-bromodaunorubicin hydrochloride (6 g) and dry sodium 2,2-bis-(4-methoxyphenoxy)-acetate (12.1 g) in acetone (1500 cc) is heated under reflux for 2 hours 30 minutes. The mixture is filtered hot over diatomaceous silica. The filtrate is concentrated to dryness under reduced pressure (20 mmHg) at 40° C. The red paste obtained is taken up in chloroform (300 cc). The resulting solution is washed with a saturated aqueous sodium bicarbonate solution (50 cc) and then with water (2×50 cc), dried over sodium sulphate, filtered and concentrated to dryness under reduced pressure (20 mmHg) at 40° C. The red solid obtained is dissolved in chloroform (15 cc) and the solution is poured over a column (height 50 cm, diameter 30 mm) containing silica gel (100 g) in chloroform. Elution is carried out with chloroform (2100 cc) containing from 2 to 5% by volume of methanol (concentration gradient), the eluate being collected in fractions of 70 cc. The fractions 16 to 28 are combined and concentrated to dryness under reduced pressure (20 mmHg) at 40° C. The red solid is dissolved in chloroform (10 cc). Diethyl ether (100 cc) is added, and the precipitate is filtered off, washed with diethyl ether (2×10 cc) and dried under reduced pressure (0.5 mmHg) at 40° C. 14-[2,2-bis(4-Methoxyphenoxy)-acetoxy]daunorubicin (0.65 g), having the following characteristics, is thus obtained:

Rf=0.6 [silica gel; methylene chloride:methanol:formic acid:water (88:15:2:1 by volume)].

Analysis % calculated: C, 62.24; H, 5.22; N, 1.69; O, 30.85. % found: C, 62.25; H, 5.15; N, 1.0.

Ethyl 2,2-bis(4-methoxyphenoxy)-acetate, from which the sodium 2,2-bis(4-methoxyphenoxy)-acetate is prepared in the usual manner, can be obtained by application of the method described by I. Minamida et al., Tetrahedron 24, 5,293 (1968), by proceeding as follows:

Sodium (5.4 g) is dissolved in absolute ethanol (160 cc). 4-Methoxyphenol (29.2 g) dissolved in absolute ethanol (20 cc) is added. The mixture is stirred for 1 hour at ambient temperature. Ethyl 2,2-dichloro-acetate (20 g) dissolved in absolute ethanol (20 cc) is then added and the mixture is heated under reflux for 20 hours. The ethanol is driven off under reduced pressure (20 mmHg) at 40° C. and the residue is taken up in diethyl ether (100 cc). The organic phase is washed with 0.1 N sodium hydroxide solution (100 cc) and with water (2×100 cc) and is then dried over sodium sulphate, filtered and concentrated to dryness under reduced pressure (20 mmHg) at 40° C. Ethyl 2,2-bis(4-methoxyphenoxy)-acetate (30 g) is thus obtained in the form of an oil.

EXAMPLE 6

A mixture of 14-bromodaunorubicin hydrochloride (5 g) and dry sodium 2,2-diethylthio-acetate (6.25 g) in acetone (3500 cc) is heated under reflux for 2 hours whilst stirring. After cooling, the reaction mixture is filtered and the solid is washed with acetone (2×50 cc). The filtrate is concentrated under reduced pressure (20 mmHg) at 40° C. The residue is suspended in methylene chloride (100 cc), filtered off and washed with methylene chloride (3×30 cc). The red solid obtained is dissolved in chloroform containing 5% by volume of methanol (150 cc). The solution is washed with a 5% (w/v) aqueous sodium bicarbonate solution (2×150 cc) with a saturated aqueous sodium chloride solution (150 cc) and with distilled water (150 cc). The organic phase is dried over sodium sulphate, filtered and concentrated to about 50 cc under reduced pressure (20 mmHg) at 30° C. Diethyl ether (300 cc) is then added and the precipitate is filtered off and washed with diethyl ether (3×50 cc). The red solid is dried under reduced pressure (0.5 mmHg) at 40° C. to give 14-(2,2-diethylthioacetoxy)-daunorubicin (2 g) having the following characteristics:

$[\alpha]_D^{20} = +170° \pm 9°$ (c=0.398, chloroform)

Rf=0.32 [silica gel; methylene chloride:methanol:-formic acid:water (88:15:2:1 by volume)].

Analysis: % calculated: C, 56.16; H, 5.57; N, 1.98; O, 27.20; S, 9.09. % found: C, 56.40; H, 5.65; N, 2.06; S, 8.89.

Ethyl 2,2-diethylthio-acetate, from which sodium 2,2-diethylthio-acetate is prepared in accordance with the usual methods, can be obtained in accordance with the method described by I. Minamida et al., Tetrahedron 24, 5,293 (1968).

EXAMPLE 7

A mixture of 14-bromodaunorubicin hydrochloride (5 g) and dry sodium 2,2-diphenylthio-acetate (9.2 g) in acetone (3500 cc) is heated under reflux for 2 hours whilst stirring. The reaction mixture is filtered hot and the solid is washed with acetone (2×50 cc). The filtrate is concentrated to dryness under reduced pressure (20 mmHg) at 40° C. The residue is suspended in methylene chloride (100 cc), filtered off and washed with methylene chloride (3×20 cc). The red solid obtained is dissolved in chloroform containing 10% by volume of methanol (300 cc). The resulting solution is washed with a 5% (w/v) aqueous sodium bicarbonate solution (2×150 cc), with a saturated aqueous sodium chloride solution (150 cc) and with distilled water (150 cc). The organic phase is dried over sodium sulphate, filtered and concentrated to about 50 cc under reduced pressure (20 mmHg) at 30° C. Diethyl ether (300 cc) is added and the precipitate is filtered off and washed with diethyl ether (3×50 cc). The red solid is dried under reduced pressure (0.5 mmHg) at 40° C. to give 14-(2,2-diphenylthio-acetoxy)daunorubicin (2.45 g) having the following characteristics:

$[\alpha]_D^{20} = +156° \pm 12°$ (c=0.331, chloroform)

Rf=0.36 [silica gel; methylene chloride:methanol:-formic acid:water (88:15:2:1 by volume)].

Analysis: % calculated: C, 61.41 H, 4.90; N, 1.75; O, 23.93; S, 8.00. % found: C, 61.15; H, 4.99; N, 1.54; S, 8.93.

Ethyl 2,2-diphenylthio-acetate, from which sodium 2,2-diphenylthio-acetate is prepared in accordance with the usual methods, can be obtained in accordance with the method of I. Minamida et al., Tetrahedron 24, 5,293, (1968).

EXAMPLE 8

A mixture of 14-bromodaunorubicin hydrochloride (5.2 g) and dry sodium 1,3-dioxolan-2-carboxylate (5.2 g) in acetone (2500 cc) is heated under reflux for 24 hours whilst stirring. After cooling, the reaction mixture is filtered. The filtrate is concentrated to dryness under reduced pressure (20 mmHg) at 40° C. The amorphous red product obtained is taken up in refluxing methylene chloride (300 cc). The red solution obtained is cooled to 0° C. The precipitate obtained is filtered off and washed with methylene chloride (2×25 cc). A red solid (1.93 g) is thus obtained, which is dissolved in boiling methanol (50 cc). After filtering off a slight amount of insoluble matter, the methanol solution is cooled to 0° C. The red precipitate is filtered off and washed with cold methanol (2×5 cc). The red solid is dried under reduced pressure (0.5 mmHg) at 40° C. 14-[(1,3-Dioxolan-2-yl)carbonyloxy]daunorubicin (0.74 g) is thus obtained in the form of a salt of 1,3-dioxolan-carboxylic acid, having the following characteristics:

$[\alpha]_D^{20} = +108° \pm 11°$ [c=0.3; chloroform:methanol (8:2 by volume)].

Rf=0.58 [silica gel; methylene chloride:methanol:-formic acid:water (88:15:2:1 by volume)].

Analysis: % calculated: C, 55.19; H, 5.16; N, 1.84; O, 37.81. % found: C, 55.0; H, 5.2; N, 1.8.

Ethyl 1,3-dioxolan-2-carboxylate, from which sodium 1,3-dioxolan-2-carboxylate can be prepared in accordance with the usual methods, can be obtained in accordance with the method described by I. Minamida et al., Tetrahedron 24, 5,293 (1968), on proceeding as follows:

A mixture of ethyl 2,2-diethoxy-acetate (96 g), ethylene glycol (40 g) and boron trifluoride etherate (50 g) in cyclohexane (300 cc) is heated under reflux for 4 days whilst stirring. After cooling, the mixture is poured onto crushed ice (200 g) and neutralised with solid sodium bicarbonate. The mixture is extracted with diethyl ether (3×250 cc), and the ether phase is washed with water (2×100 cc) and dried over sodium sulphate. It is then concentrated to dryness under reduced pressure (20 mmHg) at 30° C. Distillation under a pressure of 35 mmHg gives an oil (49 g) which distils at 101°–104° C. and contains 15 % of ethyl 2,2-diethoxy-acetate. The oil thus obtained is again reacted under the same conditions for 2 days. After identical treatment, ethyl 1,3-dioxolan-2-carboxylate (18.5 g; b.p. 95° C./35 mmHg) is obtained.

EXAMPLE 9

A mixture of 14-bromodaunorubicin hydrochloride (4 g) and dry sodium 1,3-dithiolan-2-carboxylate (3.84 g) in acetone (4000 cc) is heated under reflux for 4 hours 30 minutes whilst stirring. The mixture is then concentrated to dryness under reduced pressure (20 mmHg). The residue is taken up in chloroform (300 cc) and the solution is washed successively with water (100 cc) and 0.01 N hydrochloric acid (100 cc). The acid aqueous solution is adjusted to pH 8.2 with a saturated aqueous sodium bicarbonate solution and is then extracted with chloroform (3×100 cc). The organic solution is dried over sodium sulphate. After filtering and concentrating under reduced pressure (20 mmHg), the product obtained is dissolved in methylene chloride (10 cc) and the solution is poured over a column (diameter 2.4 cm, height 40 cm) containing silica gel (125 g) in methylene chloride. Elution is carried out successively with methylene chloride (1000 cc) and then with methylene chloride (2000 cc) containing from 3 to 10% by volume of methanol (concentration gradient), the eluate being collected in fractions of 125 cc. Fractions 17 to 24 are combined and concentrated to dryness under reduced pressure (20 mmHg). The product obtained is dissolved in a mixture of chloroform and methanol (98.2 by volume; 100 cc). The solution is cooled to 0° C. and a 1.085 N solution of dry hydrogen chloride in dioxan (2.76 cc) is added. The mixture is filtered and the red solid precipitate is dried under reduced pressure (0.5 mmHg) at 40° C. 14-[(1,3-Dithiolan-2-yl)carbonyloxy]-daunorubicin hydrochloride (1.25 g), having the following characteristics, is thus obtained:

$[\alpha]_D^{20} = -136.6° \pm 7.5°$ (c=0.505, water)

Rf=0.29 [silica gel; methylene chloride:methanol:-formic acid:water (88:15:2:1 by volume)].

Analysis: % calculated: C, 52.28; H, 4.81; Cl, 4.98; N, 1.97; O, 26.96; S, 9.60. % found: C, 51.4; H, 5.2; Cl, 5.1; N, 1.76; S, 8.7.

Sodium 1,3-dithiolan-2-carboxylate is prepared by the usual methods from 1,3-dithiolan-carboxylic acid, which can be obtained in accordance with the method of I. Minamida et al., Tetrahedron, 24, 5,293 (1968).

EXAMPLE 10

A mixture of 14-bromodaunorubicin hydrochloride (5 g) and dry sodium 1,3-dithiane-2-carboxylate (5.8 g) in acetone (1500 cc) is heated under reflux for 6 hours whilst stirring. After cooling, the reaction mixture is filtered. On the one hand, the precipitate is washed with a mixture of water and acetone (1:1 by volume; 4×50 cc) and then with distilled water (50 cc). After drying in air, a red powder (2.57 g) is obtained. On the other hand, the filtrate is concentrated to dryness under reduced pressure (20 mmHg) at 40° C. The resulting solid is suspended in chloroform (200 cc), and the precipitate is filtered off and washed with chloroform (50 cc), methanol (50 cc), ethyl acetate (50 cc) and diethyl ether (50 cc). The red solid is dried under reduced pressure (0.5 mmHg) at 20° C. A red powder (3.28 g), which in thin layer chromatography on silica gel ]solvent; methylene chloride:methanol:formic acid:water (88:15:2:1 by volume)] is identical to the first precipitate isolated, is thus obtained. The second solid, which is slightly purer, is suspended in methanol (100 cc) and treated with a 1.06 N solution of dry hydrogen chloride in dioxan (4.5 cc). The limpid red solution obtained is treated with diethyl ether (250 cc). The resulting precipitate is filtered off and is washed with ethyl acetate (2×50 cc) and with diethyl ether (50 cc). The red solid is dried under reduced pressure (0.5 mmHg) at 40° C. to give 14-[(1,3-dithian-2-yl)carbonyloxy]daunorubicin hydrochloride (2.4 g) having the following characteristics:

$[\alpha]_D^{20} = +226.4° \pm 3.5°$ (c=0.5, methanol)

Rf=0.44 [silica gel; methylene chloride:methanol:formic acid:water (88:15:2:1 by volume)].

Analysis: % calculated: C, 52.92; H, 5.00; Cl, 4.88; N, 1.93; O, 26.44; S, 8.85. % found: C, 52.39; H, 5.25; Cl, 5.16; N, 1.92; S, 8.86.

1,3-Dithiane-2-carboxylic acid, from which sodium 1,3-dithiane-2-carboxylate is prepared in accordance with the usual methods, can be obtained in accordance with the method of I. Minamida et al., Tetrahedron 24, 5,293 (1968).

EXAMPLE 11

A mixture of 14-bromodaunorubicin hydrochloride (6 g) and dry sodium 1,3-oxathiolan-2-carboxylate (6 g) in acetone (3000 cc) is heated under reflux for 24 hours whilst stirring. After cooling, the reaction mixture is filtered. The filtrate is concentrated to dryness under reduced pressure (20 mmHg) at 40° C. The red amorphous product obtained is taken up in ice-water (150 cc) and extracted with chloroform (2×150 cc). The aqueous phase is brought to pH 8 with a 5% (w/v) aqueous bicarbonate solution. It is then extracted with chloroform (3×100 cc), dried over sodium sulphate, filtered and concentrated to dryness under reduced pressure (20 mmHg) at 20° C. A red powder (3.5 g) is thus obtained. The solid is dissolved in chloroform (15 cc) and the solution is poured over a column (diameter 3.25 cm, height 25 cm) containing silica gel (100 g) in chloroform. Elution is carried out with chloroform containing 6% by volume of methanol (1500 cc), and the eluate is collected in fractions of 150 cc. The 10 first fractions are combined and concentrated to dryness under reduced pressure (20 mmHg) at 40° C. The solid obtained is dissolved in chloroform (15 cc) and the solution is poured over a column (diameter 2 cm, height 40 cm) containing silica gel (60 g). Elution is carried out with chloroform containing 5% by volume of methanol (1800 cc), and the eluate is collected in fractions of 100 cc. Fractions 11 to 18 are combined and concentrated to dryness under reduced pressure (20 mmHg) at 40° C. The product obtained is dissolved in chloroform (20 cc) and a 0.32 N solution of dry hydrogen chloride in dioxan (1.3 cc) is added. Diethyl ether (20 cc) is then added and the resulting red solid is separated by filtration, washed with diethyl ether (2×10 cc) and dried under reduced pressure (1 mmHg) at 40° C. 14-[(1,3-Oxathiolan-2-yl)carbonyloxy]daunorubicin hydrochloride (0.765 g), having the following characteristics, is thus obtained:

$[\alpha]_D^{20} = +217° \pm 12°$ [c=0.2, methanol]

Rf=0.37 [silica gel; methylene chloride:methanol:formic acid:water (88:15:2:1 by volume)].

Analysis: % calculated: C, 53.49; H, 4.92; Cl 5.09; N, 2.01; O, 29.88; S, 4.61. % found: C, 53.10; H, 4.7; Cl, 4.85; N, 1.70; S, 4.59.

n-Butyl 1,3-oxathiolan-2-carboxylate, from which the sodium 1,3-oxathiolan-2-carboxylate is prepared in accordance with the usual methods, can be obtained by proceeding as follows:

A mixture of n-butyl glyoxylate (32 g), mercaptoethanol (22 g) and boron trifluoride etherate (36 cc) in benzene (300 cc) is stirred at ambient temperature for 16 hours. The mixture is poured onto crushed ice (300 g), neutralised with solid sodium bicarbonate and extracted with diethyl ether (4×200 cc). The ether phase is washed with distilled water (300 cc), dried over sodium sulphate and filtered. It is concentrated to dryness under reduced pressure (20 mmHg) at 30° C. A liquid (35 g) is obtained, which after distillation gives an oil (20 g; b.p. 83° C./0.3 mmHg). This oil is poured onto a column (diameter 3.5 cm, height 60 cm) containing silica gel (300 g) in petroleum ether (distillation range 40°-60° C.). Elution is carried out successively with petroleum ether (distillation range 40°-60° C.; 1000 cc) and then with petroleum ether (distillation range 40°-60° C.) containing 5% by volume of ethyl acetate (2000 cc), and the eluate is collected in fractions of 500 cc. Fractions 3 and 4 are combined and concentrated to dryness under reduced pressure (20 mmHg) at 30° C. n-Butyl 1,3-oxathiolan-2-carboxylate (13 g) is thus obtained.

n-Butyl glyoxylate can be prepared in accordance with F. J. Wolf and J. Weijlard, Org. Synth. 35, 18, (1955).

EXAMPLE 12

A mixture of 14-bromodaunorubicin hydrochloride (1.78 g) and sodium 2,2-diethoxy-propionate (2.55 g) in acetone (400 cc) and ethanol (40 cc) is heated under reflux for 6 hours whilst stirring. The reaction mixture is then allowed to cool, filtered and concentrated to dryness under reduced pressure (20 mmHg) at 40° C. The residue is taken up in chloroform (100 cc), the solution filtered, washed with an aqueous buffer solution (150 cc) at pH 7 [prepared from a 0.1 M aqueous mono-potassium phosphate solution (500 cc) and a 0.1 N sodium hydroxide solution (291 cc)], the buffer solution is extracted with chloroform (2×100 cc), the three chloroformic solutions are combined and washed with a saturated aqueous sodium chloride solution (100 cc) and the saturated aqueous solution is extracted with chloroform (50 cc). The combined organic phases are dried over sodium sulphate, filtered and concentrated to dryness under reduced pressure (20 mmHg) at 30° C. The residue is dissolved in chloroform (15 cc) and the solution is poured onto a column (diameter 3 cm, height 36 cm) containing silica gel (120 g) in chloroform. Elution is carried out successively with chloroform (1500 cc) and then with chloroform containing from 5 to 10% by volume of methanol (2250 cc) (concentration gradient), and the eluate is collected in fractions of 100 cc. Fractions 17 to 27 are combined and concentrated to dryness under reduced pressure (20 mmHg) at 30° C. The product obtained is dissolved in chloroform (50 cc). A 1.06 N solution of dry hydrogen chloride in dioxan (2 cc) is added, and the resulting red solid is filtered off and dried under reduced pressure (0.5 mmHg) at 40° C. 14-(2,2-Diethoxy propanoyloxy)daunorubicin hydrochloride (1.46 g), having the following characteristics, is thus obtained:

$[\alpha]_D^{20} = +191.2° \pm 5°$ (c=0.3, methanol)

Rf=0.48 [silica gel; methylene chloride:methanol:formic acid:water (88:15:2:1 by volume)].

Analysis: % calculated: C, 56.39 H, 5.85; Cl, 4.90; H, 1.93; O, 30.93. % found: C, 55.96; H, 5.85; Cl, 5.01; N, 1.91.

Sodium 2,2-diethoxy-propionate can be obtained from ethyl 2,2-diethoxy-propionate in accordance with the usual methods.

Ethyl 2,2-diethoxy-propionate can be obtained in accordance with the method of C. G. Wermuth and H. Marx, Bull. Soc. Chim. France 732, (1964).

EXAMPLE 13

A mixture of 14-bromodaunorubicin hydrochloride (5 g) and dry sodium 2-phenyl-1,3-dithiolan-2-carboxylate (5 g) in acetone (2300 cc) is heated under reflux for 18 hours whilst stirring. The reaction mixture is filtered hot and the filtrate is concentrated to dryness under reduced pressure (20 mmHg) at 40° C. The red varnish is taken up in methylene chloride (500 cc). The organic solution is washed with a 5% (w/v) aqueous sodium bicarbonate solution (2×100 cc) and with distilled water (250 cc), and is then dried over sodium sulphate, filtered and concentrated to dryness under reduced pressure (20 mmHg) at 40° C. The solid obtained is dissolved in chloroform (15 cc) and the solution is poured onto a column (diameter 2.5 cm) containing silica gel (100 g) in chloroform. Elution is carried out successively with chloroform (2000 cc) and with chloroform containing from 1 to 5% by volume of methanol (4000 cc) (concentration gradient), and the eluate is collected in fractions of 100 cc. Fractions 41 to 55 are combined and concentrated to dryness under reduced pressure (20 mmHg) at 40° C. The product obtained is dissolved in chloroform (30 cc). A 0.91 N solution of dry hydrogen chloride in dioxan (3.5 cc) is added. The resulting red precipitate is filtered off and dried under reduced pressure (0.5 mmHg) at 40° C. 14-[(2-Phenyl-1,3-dithiolan-2-yl)carbonyloxy]daunorubicin hydrochloride (2.23 g), having the following characteristics, is thus obtained:

$[\alpha]_D^{20} = +209° \pm 9°$ (c=0.4 methanol)

Rf=0.35 [silica gel; methylene chloride:methanol:formic acid:water (88:15:2:1 by volume)].

Analysis % calculated: C, 56.38; H, 4.86; Cl, 4.50; N, 1.78; O, 24.35; S, 8.13. % found: C, 56.68; H, 5.2; Cl, 4.62; N, 1.80; S, 7.82.

Sodium 2-phenyl-1,3-dithiolan-2-carboxylate can be prepared from ethyl 2-phenyl-1,3-dithiolan-2-carboxylate in accordance with the usual methods.

Ethyl 2-phenyl-1,3-dithiolan-2-carboxylate can be prepared in accordance with the method described by I. Minamida et al., Tetrahedron 24, 5, 293 (1968).

EXAMPLE 14

14-(2,2-Diethoxy-acetoxy)daunorubicin hydrochloride (3.8 g) is dissolved in distilled water (150 cc). The solution is adjusted to pH 8 with a saturated aqueous sodium bicarbonate solution and is then extracted with chloroform. The extract is dried over sodium sulphate, filtered and concentrated to dryness under reduced pressure (20 mmHg). 14-(2,2-Diethoxy-acetoxy)-daunorubicin (2.5 g) is thus obtained, and is dissolved in chloroform (162 cc). Diethyl ether (65 cc) is added; the temperature of the mixture rises to 32° C. Trifluoroacetic anhydride (3.85 cc) is added immediately in one lot. The mixture is stirred for 5 minutes and is then washed with water (3×250 cc), dried over sodium sulphate, filtered and concentrated to dryness under reduced pressure (20 mmHg).

The product obtained is dissolved in chloroform (10 cc) and the solution is poured onto a column (diameter 3 cm, height 36 cm) containing silica gel (120 g) in chloroform. Elution is carried out successively with chloroform (500 cc) and then with chloroform containing from 1 to 10% by volume of ethyl acetate (4000 cc) (concentration gradient), and the eluate is collected in fractions of 100 cc. Fractions 16 to 45 are combined and concentrated to dryness under reduced pressure (20 mmHg). The product obtained is dissolved in chloroform (10 cc) and is precipitated by adding petroleum ether (b.p. 40°–65° C.; 20 cc). The red solid is filtered off, washed with petroleum ether and dried under reduced pressure (0.5 mmHg) at 40° C.

14-(2,2-Diethoxy-acetoxy)-N-trifluoroacetyl-daunorubicin (0.9 g), having the following characteristics, is thus obtained:

$[\alpha]_D^{20} = +233.7° \pm 9°$ (c=0.385, chloroform)

Rf=0.57 [silica gel; methylene chloride:methanol (93:7 by volume)].

Analysis: % calculated: C, 54.62; H, 4.98; F, 1.82; N, 7.40; O, 31.18. % found: C, 54.3; H, 4.95; F, 1.8; N, 6.9.

EXAMPLE 15

A mixture of 14-bromodaunorubicin hydrochloride (7 g) and dry sodium 2,2-bis(4-methylphenoxy)acetate (10.7 g) in acetone (700 cc) is heated under reflux with stirring for 3½ hours. The mixture is then allowed to cool to 40° C. and filtered through diatomaceous silica. The filtrate is concentrated under reduced pressure (20 mmHg) at 35° C. The paste obtained is dissolved in chloroform (500 cc) and the solution obtained is washed three times with distilled water (200 cc each time). The organic phase is dried over anhydrous sodium sulphate, filtered, and concentrated to dryness under reduced pressure (20 mmHg) at 35° C. The red solid obtained is taken up in diethyl ether (200 cc) and the mixture is filtered. The residue is washed twice with ethyl acetate (150 cc each time) and twice with diethyl ether (150 cc each time) and then dried under reduced pressure (0.5 mmHg) at 25° C. 14-[2,2-Bis(4-methylphenoxy)acetoxy]daunorubicin is thus obtained as its 2,2-bis(4-methylphenoxy)acetate (6.5 g). This red solid is dissolved in chloroform (150 cc). The solution is cooled to 10° C. and a dry 0.465 N solution of hydrogen chloride in dioxan (13.5 cc) is then added. The red precipitate is filtered off and washed twice with ethyl acetate (50 cc each time) and twice with diethyl ether (50 cc each time). The red solid is dried under reduced pressure (0.5 mmHg) at 40° C. The hydrochloride of 14-[2,2-bis(4-methylphenoxy)acetoxy]daunorubicin (3.5 g) is thus obtained having the following characteristics:

$[\alpha]_D^{20} = +238° \pm 12°$ (c=0.299, methanol)

Rf=0.4 (in chromatography on a silica gel plate, eluting with methylene chloride-methanol-formic acid-water, 88:15:2:1 by volume).

Analysis: % calculated: C, 61.91; H, 5.31; Cl, 4.25; N, 1.68; O, 26.85. % found: C, 61.52; H, 5.22; Cl, 4.81; N, 1.61.

The ethyl-2,2-bis(4-methylphenoxy)acetate from which the sodium 2,2-bis(4-methylphenoxy)acetate used as starting material is prepared by conventional methods, can be obtained in the following manner:

Sodium (5.7 g) is dissolved in ethanol (160 cc), and a solution of para-cresol (27 g) in ethanol (20 cc) is added. The mixture is stirred for 1 hour at 20° C. and ethyl dichloroacetate (20 g) in solution in ethanol (20 cc) is then added. The mixture is heated under reflux for 20 hours and then allowed to cool. The white precipitate obtained is filtered off and the filtrate is concentrated to dryness under reduced pressure (20 mmHg) at 40° C. The oil thus obtained is taken up in diethyl ether (300 cc) and washed twice with N sodium hydroxide solution (100 cc each time) and twice with distilled water (100 cc each time). The ethereal phase is then dried over anhydrous sodium sulphate, filtered, and concentrated to dryness under reduced pressure (20 mmHg) at 40° C. Ethyl 2,2-bis(4-methylphenoxy)acetate (29 g) is thus obtained as a yellow oil.

EXAMPLE 16

A mixture of 14-bromodaunorubicin hydrochloride (3 g) and dry sodium 2,2-bis(4-methylthiophenoxy)acetate (4.7 g) in acetone (300 cc) is heated under reflux with stirring for 1 hour and then allowed to cool to 35° C. The reaction mixture is then filtered through diatomaceous silica and the filtrate is concentrated under reduced pressure (20 mmHg) at 35° C. The red paste obtained is taken up in diethyl ether (250 cc) and the mixture is filtered. The red solid obtained is washed three times with ethyl acetate (100 cc each time) and three times with diethyl ether (100 cc each time). The red powder obtained is dissolved in chloroform containing 10% methanol (700 cc) and the solution obtained is washed twice with distilled water (150 cc each time). The organic phase is then dried over anhydrous sodium sulphate, filtered, and concentrated to dryness under reduced pressure (20 mmHg) at 35° C. The red powder obtained is taken up in diethyl ether (300 cc) and the mixture is filtered. The residue is washed three times with ethyl acetate (100 cc each time) and three times with diethyl ether (100 cc each time). The red solid obtained is dried under reduced pressure (0.5 mmHg) at 25° C. 14-[2,2-Bis-(4-methylthiophenoxy)acetoxy]daunorubicin as its 2,2-bis(4-methylthiophenoxy)acetate (1.5 g) is thus obtained as a red solid which is dissolved in chloroform (50 cc). The solution is cooled to 5° C. and an anhydrous 0.465 N solution of hydrogen chloride in dioxan (2.7 cc) is then added. The red precipitate is filtered off, washed three times with ethyl acetate (20 cc each time) and three times with diethyl ether (20 cc each time). The red solid is dried under reduced pressure (0.5 mmHg) at 40° C. 14-[2,2-Bis(4-methylthiophenoxy)acetoxy]daunorubicin hydrochloride (1.1 g) is thus obtained having the following characteristics:

$[\alpha]_D^{20} = +345° \pm 18°$ (c=0.172, methanol)

Rf=0.34 [chromatography on a silica gel plate eluting with methylene chloride-methanol-formic acid-water (88:15:2:1 by volume)]

Analysis: % calculated: C, 57.49; H, 4.94; Cl, 3.94; N, 1.56; O, 24.93; S, 7.14. % found: C, 57.18; H, 4.90; Cl, 4.01; N, 1.58 S, 6.78.

Ethyl 2,2-bis(4-methylthiophenoxy)acetate from which sodium 2,2-bis(4-methylthiophenoxy)acetate can be prepared by known methods, can be obtained in the following manner:

Sodium (3.54 g) is dissolved in methanol (140 cc) and a solution of 4-methylthiophenol (21.8 g) in methanol (25 cc) is added. The mixture is stirred for 1 hour at 20° C. and a solution of ethyl dichloroacetate (12.5 g) in methanol (30 cc) is then added. The mixture is allowed to cool, the white precipitate obtained is filtered off, and the filtrate is concentrated to dryness under reduced pressure (20 mmHg) at 40° C. The oil obtained is taken up in diethyl ether (250 cc) and washed four times with N sodium hydroxide solution (50 cc each time) and four times with distilled water (50 cc each time). The ethereal phase is dried over anhydrous sodium sulphate, filtered, treated with animal charcoal, filtered and concentrated to dryness under reduced pressure (20 mmHg) at 40° C. Ethyl 2,2-bis(4-methylthiophenoxy)acetate (18 g) is thus obtained as a yellow oil.

The present invention includes within its scope pharmaceutical compositions which comprise, as active ingredient, at least one daunorubicin derivative of general formula I, or—when $R_2$ represents a hydrogen atom—a nontoxic acid addition salt thereof, in association with a compatible pharmaceutical carrier, which may be inert or physiologically active. The compositions may be in any of the forms appropriate for the envisaged method of administration Parenteral administration, especially intravenous administration is the preferred method.

The compositions according to the invention for parenteral administration include sterile aqueous or nonaqueous solutions, suspensions or emulsions. Examples of non-aqueous solvents or vehicles are propylene glycol, polyethylene glycol, vegetable oils such as olive oil and injectable organic esters such as ethyl oleate. These compositions can also contain adjuvants such as preserving, wetting, emulsifying and dispersing agents. They may be sterilized by, for example, filtration through a bacteria-retaining filter, by incorporation in the compositions of sterilizing agents or by irradiation. They may also be manufactured in the form of sterile solid compositions which can be dissolved or dispersed, at the time of use, in sterile water or some other sterile injectable medium.

The daunorubicin derivatives of general formula I and—when appropriate—their non-toxic acid addition salts are, more particularly, used in the treatment of cancers (such as, for example, of acute leukaemias and of sarcomas) at daily doses which are generally between 1 and 5 mg/kg body weight, administered intravenously, in the case of an adult. In general the physician will decide the posology considered appropriate, taking into account the age and weight and other factors intrinsic to the patient being treated.

The following Example illustrates pharmaceutical compositions according to the invention.

EXAMPLE 17

A solution containing 14-(2,2-diethoxy-acetoxy)-daunorubicin hydrochloride (28.1 mg/cc) is prepared by dissolving the compound (4.215 g) in a non-pyrogenic physiological solution in sufficient amount to give 150 cc. The solution obtained is divided aseptically between ampoules in an amount of 3 cc per ampoule. The ampoules are sealed and each contain 80 mg of 14-(2,2-diethoxy-acetoxy)daunorubicin (base).

We claim:

1. A daunorubicin derivative of the formula

[Structural formula showing daunorubicin derivative with substituents: O, OH, COCH₂OCOR₁, OH, CH₃O, O, OH, O—CH—CH₂—CH—CHOH—CH—CH₃, NH—R₂, with O bridge]

wherein $R_1$ represents a group of the formula $$-\underset{R_4}{\overset{X_1-R_3}{\underset{|}{C}}}\diagdown_{X_2-R_3}$$

in which (i) $X_1$ and $X_2$ both represent oxygen or both represent sulphur and the symbols $R_3$ each represent alkyl of 1 through 4 carbon atoms, phenyl or phenyl-substituted in the para-position by methyl, methoxy or methylthio, or together form an alkylene radical of 2 through 4 carbon atoms, or (ii) one of $X_1$ and $X_2$ represents oxygen and the other represents sulphur and the symbols $R_3$ together form an alkylene radical of 2 through 4 carbon atoms, and $R_4$ represents hydrogen, alkyl of 1 through 4 carbon atoms or phenyl, and $R_2$ represents hydrogen or trifluoroacetyl, or a non-toxic pharmaceutically acceptable acid addition salt of said derivative in which $R_2$ represents hydrogen.

2. A daunorubicin derivative according to claim 1 wherein $X_1$ and $X_2$ both represent oxygen atoms or both represent sulphur atoms and the symbols $R_3$ each represent alkyl of 1 through 4 carbon atoms, phenyl or—when $X_1$ and $X_2$ represent sulphur—together form an alkylene radical of 2 through 4 carbon atoms, and $R_4$ represents hydrogen or a non-toxic pharmaceutically acceptable acid addition salt of said derivative in which $R_2$ represents hydrogen.

3. A daunorubicin derivative according to claim 1 wherein $X_1$ and $X_2$ both represent oxygen or both represent sulphur and the symbols $R_3$ each represent alkyl of 1 through 4 carbon atoms, phenyl or phenyl-substituted in the para-position by methoxy, or together form an alkylene radical of 2 or 3 carbon atoms, or one of the symbols $X_1$ and $X_2$ represents oxygen and the other represents sulphur and the symbols $R_3$ together form an alkylene radical of 2 or 3 carbon atoms, and $R_4$ represents hydrogen, methyl or phenyl, and non-toxic pharmaceutically acceptable acid addition salt of said derivative in which $R_2$ represents hydrogen.

4. A daunorubicin derivative according to claim 1 wherein $X_1$ and $X_2$ both represent oxygen or both represent sulphur and the symbols $R_3$ each represent alkyl of 1 through 4 carbon atoms, or phenyl or p-methoxyphenyl, or together form an alkylene radical of 2 or 3 carbon atoms, or one of $X_1$ and $X_2$ represents oxygen and the other represents sulphur and the symbols $R_3$ together form an alkylene radical of 2 or 3 carbon atoms, $R_4$ represents hydrogen, and $R_2$ represents hydrogen, or a non-toxic pharmaceutically acceptable acid addition salt thereof.

5. A daunorubicin derivative according to claim 1 wherein $X_1$ and $X_2$ both represent oxygen or both represent sulphur and the symbols $R_3$ each represent alkyl of 1 through 4 carbon atoms, phenyl or phenyl-substituted in the para-position by methyl, methoxy, or methylthio or together form an alkylene radical of 2 or 3 carbon atoms, or one of the symbols $X_1$ and $X_2$ represents oxygen and the other represents sulphur and the symbols $R_3$ together form an alkylene radical of 2 or 3 carbon atoms, and $R_4$ represents hydrogen, methyl or phenyl, or a nontoxic pharmaceutically acceptable acid addition salt of said derivative in which $R_2$ represents hydrogen.

6. A daunorubicin derivative according to claim 1 wherein $X_1$ and $X_2$ both represent oxygen or both represent sulphur and the symbols $R_3$ each represent alkyl of 1 through 4 carbon atoms, or phenyl, p-methylphenyl, p-methoxyphenyl, or p-methylthiophenyl or together form an alkylene radical of 2 or 3 carbon atoms, or one of $X_1$ and $X_2$ represents oxygen and the other represents sulphur and the symbols $R_3$ together form an alkylene radical of 2 or 3 carbon atoms, $R_4$ represents hydrogen, and $R_2$ represents hydrogen or a non-toxic pharmaceutically acceptable acid addition salt thereof.

7. The daunorubicin derivative according to claim 1 which is 14-(2,2-diethoxy-acetoxy)daunorubicin or a non-toxic pharmaceutically acceptable acid addition salt thereof.

8. The daunorubicin derivative according to claim 1 which is 14-(2,2-dibutoxy-acetoxy)daunorubicin or a non-toxic pharmaceutically acceptable acid addition salt thereof.

9. The daunorubicin derivative according to claim 1 which is 14-(2,2-diphenoxy-acetoxy)daunorubicin or a non-toxic pharmaceutically acceptable acid addition salt thereof.

10. The daunorubicin derivative according to claim 1 which is 14[2,2-bis(4-methoxyphenoxy)acetoxy]-daunorubicin or a non-toxic pharmaceutically acceptable acid addition salt thereof.

11. The daunorubicin derivative according to claim 1 which is 14-(2,2-diethylthio-acetoxy)daunorubicin or a non-toxic pharmaceutically acceptable acid addition salt thereof.

12. The daunorubicin derivative according to claim 1 which is 14-(2,2-diphenylthio-acetoxy)daunorubicin or a non-toxic pharmaceutically acceptable acid addition salt thereof.

13. The daunorubicin derivative according to claim 1 which is 14-[(1,3-dioxolan-2-yl)carbonyloxy]daunorubicin or a non-toxic pharmaceutically acceptable acid addition salt thereof.

14. The daunorubicin derivative according to claim 1 which is 14-[(1,3-dithiolan-2-yl)carbonyloxy]-daunorubicin or a non-toxic pharmaceutically acceptable acid addition salt thereof.

15. The daunorubicin derivative according to claim 1 which is 14-[(1,3-dithian-2-yl)carbonyloxy]daunorubicin or a non-toxic pharmaceutically acceptable acid addition salt thereof.

16. The daunorubicin derivative according to claim 1 which is 14-[(1,3-oxathiolan-2-yl)carbonyloxy]-daunorubicin or a non-toxic pharmaceutically acceptable acid addition salt thereof.

17. The daunorubicin derivative according to claim 1 which is 14-[2,2-bis(4-methylphenoxy)acetoxy]-daunorubicin or a non-toxic pharmaceutically acceptable acid addition salt thereof.

18. The daunorubicin derivative according to claim 1 which is 14-[2,2-bis(4-methylthiophenoxy)acetoxy]-daunorubicin or a non-toxic pharmaceutically acceptable acid addition salt thereof.

19. A pharmaceutical composition for parenteral administration which comprises a therapeutically effective amount of a daunorubicin derivative of the formula specified in claim 1 or a nontoxic pharmaceutically acceptable acid addition salt of a said derivative in which $R_2$ represents hydrogen, in association with a sterile compatible injectable pharmaceutical carrier.

20. The pharmaceutical composition of claim 19 wherein said daunorubicin derivative is present in an amount from about 1 to about 5 mg/kg of body weight of the subject to whom said derivative is administered.

* * * * *